United States Patent [19]

Ames et al.

[11] Patent Number: 5,004,593
[45] Date of Patent: Apr. 2, 1991

[54] HEXAMETHYLMELAMINE FORMULATION EXHIBITING REDUCED NEUROTOXICITY

[75] Inventors: Matthew M. Ames; John S. Kovach, both of Rochester, Minn.

[73] Assignee: Mayo Foundation for Medical Education and Research, Rochester, Minn.

[21] Appl. No.: 339,481

[22] Filed: Apr. 17, 1989

[51] Int. Cl.$^5$ .................... A61K 31/71; A61K 31/66; A61K 31/53; A61K 33/24

[52] U.S. Cl. ........................ 424/10; 514/34; 514/110; 514/245; 424/649

[58] Field of Search ................. 424/10, 649; 514/245, 514/34, 110

[56] References Cited

U.S. PATENT DOCUMENTS 32,393   4/1887   Wretlind et al. .................... 514/219
4,784,845  11/1988  Desai et al. ............................ 424/80

OTHER PUBLICATIONS

B. J. Foster et al., Cancer Treat. Rev., 13, 197–217 (1986).
J. Louis et al., Clin. Pharmacol. Therap., 8, 55–64 (1967).
M. D'Incalci et al., Cancer Treat. Rep., 62, 2117–2119 (1978).
M. M. Ames et al., Cancer Res., 39, 5016–5021 (1979).
M. M. Ames and J. S. Kovach, Cancer Treat. Rep., 66, 1579–1581 (1982).
M. M. Ames and J. S. Kovach, "A Parenteral Formulation of Hexamethylmelamine for Use in Cancer Patients," IUPHAR 9th International Congress of Pharmacology, London, England (abstract) (1984).
R. L. Richardson et al., Proc. Amer. Assoc. Cancer Res., 27, 167 (abstract No. 662) (1986).
A. B. Borkovec and A. B. DeMilo, "Insect Chemosterilants V. Derivatives of Melamine," J. Med. Chem., 10, 457–461 (1967).
S. S. Legha et al., Cancer, 38, 27–35 (1976).
M. M. Ames and G. Powis, J. Chromatogr., 174, 245–249 (1979).
M. M. Ames et al., Life Sciences, 29, 1591–1598 (1981).
M. M. Ames et al., Cancer Res., 43, 500–504 (1983).
R. H. Blum et al., Europ. J. Cancer, 9, 195–202 (1973).
K. J. Miller et al., Cancer Chemother. Pharmacol., 15, 49–53 (1985).
R. L. Richardson et al., Proc. Amer. Assoc. Cancer Res., 27, 166 (abstract) (1986).

Primary Examiner—Jerome D. Goldberg
Attorney, Agent, or Firm—Merchant, Gould, Smith, Edell, Welter & Schmidt

[57] ABSTRACT

A method is provided for reducing the side effects of chemotherapy with hexamethylmelamine (HMM) comprising intravelously administering a stabilized solution of HMM in an aqueous lipid dispersion, so that the central nervous system toxicity associated with oral HMM administration is reduced or eliminated.

7 Claims, 2 Drawing Sheets

HEXAMETHYLMELAMINE FORMULATION EXHIBITING REDUCED NEUROTOXICITY

The s-triazine antitumor agent hexamethylmelamine (HMM) has been under laboratory and clinical evaluation for more than 20 years. In single agent clinical trials, HMM was active against a number of cancers including ovarian adenocarcinoma, metastatic small cell carcinoma of the lung, metastatic breast cancer and refractory lymphoma. HMM has been employed in a variety of combination regimens with alkylating agents such as cisplatin, cyclophosphamide, doxorubicin, vinca alkaloids, and etoposide. However, it is difficult to specifically assess the contribution of HMM to the combination regiments. See, B. J. Foster et al., Cancer Treat Rev., 13, 197 (1986), the disclosure of which is incorporated by reference herein. Nausea and vomiting are the main acute adverse effects. Delayed toxicity includes moderate anemia, thrombocytopenia, leukopenia, and a peripheral neuropathy. The peripheral neuropathy consists of parethesias, hypesthesias, motor weakness, and other sensory alterations [J. Lewis et al., Clin. Pharmacol. Therap., 8, 55 (1967)].

HMM has very limited solubility in water and non-toxic solvents, and thus has primarily been evaluated following oral administration. Low and variable plasma concentrations of parent drug were observed following oral administration of HMM to man. [M. D'Incalci et al., Cancer Treat. Rep., 62, 2117 (1978)]. The poor bioavailability of HMM following oral administration to rabbits is due to extensive first-pass metabolism rather than poor absorption from the gut [M. M. Ames et al., Cancer Res., 39, 5016 (1979)].

Several HMM formulations have been evaluated for parenteral administration. While intravenous (i.v.) administration of one specific HMM hydrochloride preparation to dogs was reported to be well-tolerated, the hydrochloride salt causes severe local irritation and phlebitis in man. A parenteral formulation in which HMM was dissolved in ethanol or dimethylacetamide and subsequently diluted in an aqueous fat emulsion (Intralipid 20% ®, Cutter Laboratories, Berkeley, CA) was successfully prepared and administered to rabbits. [M. M. Ames et al., Cancer Treat. Rep., 66, 1579 (1982)]. The need for an added organic solvent was eliminated by dissolving HMM in dilute hydrochloric acid, adding Intralipid 10% ®, and adjusting the pH with sodium bicarbonate to yield parenteral formulation which was well-tolerated by rabbits. [M. M. Ames et al, IUPHAR IXth International Congress of Pharmacology, London, England (1984)]. Administration of this formulation to cancer patients i.v. (at single doses up to 840 mg/m² or at doses of 540 mg/m² daily for five days) was reported to cause mild nausea and vomiting, and rare instances of moderate leukopenia and thrombocytopenia. [R. L. Richardson et al., Proc. Amer. Assoc. Cancer Res., 27, 166 (1986)].

Given the variety and intensity of the side effects reported upon prolonged administration of oral HMM such as neurotoxicity, a continuing need exists for techniques to reduce the side effects associated with the use of HMM to treat cancer patients.

SUMMARY OF THE INVENTION

The present invention provides a method for reducing or eliminating the peripheral neuropathy associated with hexamethylmelamine (HMM) chemotherapy. More specifically, the present method comprises the intravenous administration to a cancer patient of a stabilized solution of an effective anti-neoplastic amount of HMM in an aqueous emulsion comprising: (a) about 2-20%, preferably about 5-15% of an edible oil; (b) about 0.1-7%, preferably about 0.5-5% of a phosphatide; and about 1-10% glycerol. The emulsion will contain a major amount of water, e.g., about 50-95%, preferably about 75-90% water, and is administered at a pH of about 4.5-6, preferably at about 5-5.6. The peripheral neuropathy is reduced from the level observed when the same amount of HMM is administered orally, although the effective plasma levels of HMM are substantially higher when the present method is used. The aqueous fat emulsion acts to stabilize or maintain the HMM in solution at effective concentrations. The substitution of equivalent amounts of water, normal saline or phosphate-buffered saline for the aqueous fat emulsion resulted in immediate precipitation of the HMM.

Two Phase I clinical trials, with accompanying pharmacokinetic studies, have been conducted, wherein the present HMM formulation was intravenously administered to cancer patients with refractory tumors. The formulation was well tolerated by all patients receiving it by one-day or daily ×5 schedules. No CNS toxicity, such as peripheral neuropathy, was observed. Nausea and vomiting were the only dose-limiting toxicities. Maximally-tolerated doses on the daily ×5 schedule were approximately 850 mg/m²/day, and 630 mg/m²/day, respectively. Following intravenous administration of 540 mg/m² hexamethylmelamine, plasma elimination was best described by a three-compartment open model with terminal half-life ($t_{\frac{1}{2}}\alpha$), total body clearance ($Cl_{TB}$) and steady state volume of distribution ($Vd_{ss}$) values of 10.4 hr., 0.75 1/min/m² and 460 1/m², respectively. Twenty-four hour urinary recoveries of parent drug were less than one percent for all patients. Accumulation of hexamethylmelamine during the five-day treatment at 945 mg/m² suggested possible saturation of parent drug elimination at that dose.

As defined herein, the term "effective antineoplastic amount" of HMM is an amount which is effective to reduce or eliminate tumor bulk either when used alone or with other antineoplastic agents administered either separately or in combination with HMM infusion. Although no tumor responses were observed or expected in the Phase I clinical trial described herein, it is believed that the amounts of HMM administered would be effective when employed in appropriate combination regimens, such as those described by B. J. Foster et al., supra, and S. S. Legha et al., infra.

BRIEF DESCRIPTON OF THE DRAWINGS

DETAILED DESCRIPTION OF THE INVENTION

Figure 1:
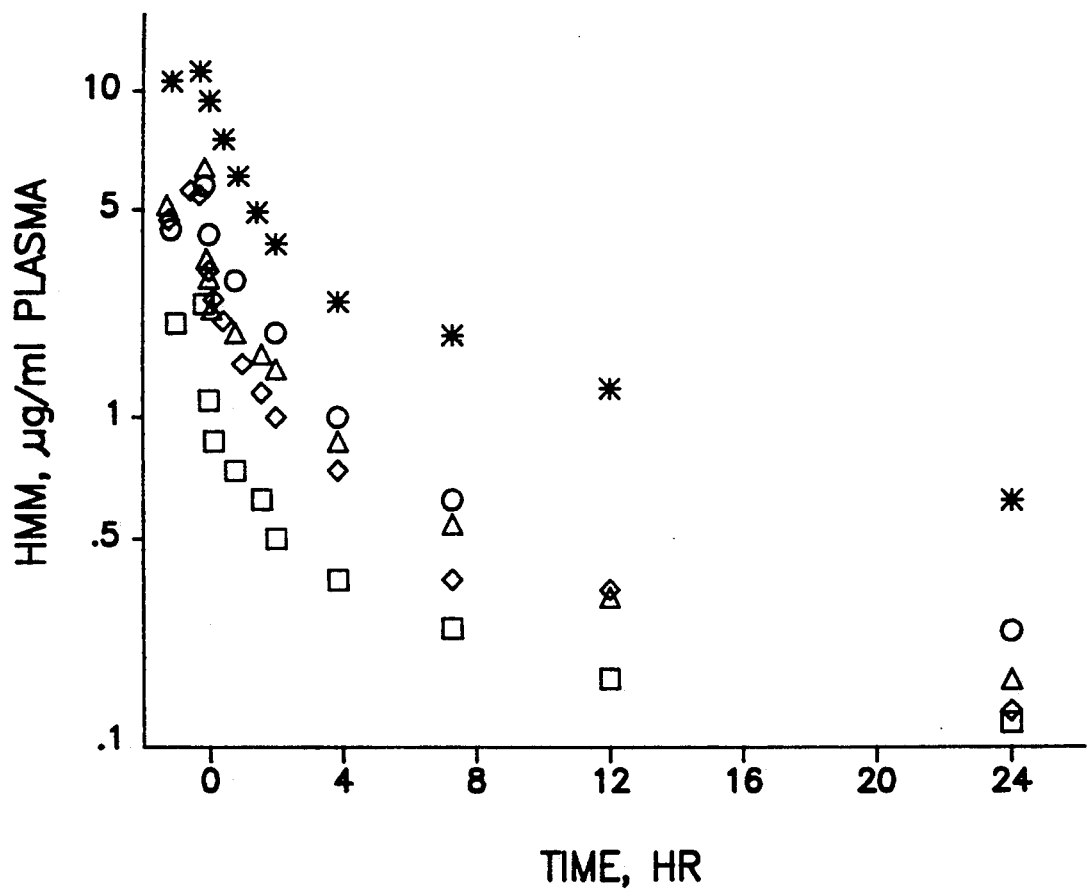
FIG. 1 is a graphical depiction of the plasma concentration-time profile for patients receiving HMM.

Hexamethylmethylmelamine [2,4,6-tris(dimethylamino)-1,3,5-triazine](HMM).

HMM is available from the Pharmaceutical Resources Branch, Developmental Therapeutics Program, Division of Cancer Treatment, National Cancer Institute, Bethesda, MD, USA. HMM can also be synthesized by the procedures of A. B. Borkovec et al., *J. Med. Chem.*, 10, 457 (1967), the disclosure of which is incorporated by reference herein.

To prepare the present formulations, HMM is first dissolved in aqueous acid and then added to an aqueous fat emulsion to a concentration so that it remains in solution when the pH of the emulsion is adjusted to the administration pH of about 4.5-6.0. The aqueous fat emulsions useful as the HMM vehicles in the present method include aqueous emulsions of one or more edible oils which are stabilized by an effective amount of a phosphatide and a nontoxic polyol or polyol ether cosolvent such as glycerol.

Edible oils useful in these emulsions include plant oils such as soybean oil, cottonseed oil, coconut oil, olive oil, sesame oil, rapeseed oil, peanut oil, safflower oil and mixtures thereof.

Phosphatide stabilizers include phosphatidylcholine, phosphatidylglycerol, phosphatidylethanolamine, phosphatidylinositol and mixtures thereof. The nontoxic natural and synthetic phosphatidylcholines are preferred for use in the present method, and include egg yolk phospholipids (ovolecithin) and soya lecithin (vegilecthin), as well as synthetic phosphatides such as dipalmitoyl phosphatidylcholine and dimyristoyl phosphatidylcholine. One commercially-available aqueous lipid emulsion is Intralipid 10% ® (Cutter Laboratories, Berkeley, CA) which contains, in water, by weight, 10% soybean oil, 1.2% egg yolk phospholipids, and 2.25% glycerol (pH $\geq$ 8.01).

Preferably, the HMM formulation is prepared by dissolving HMM in a dilute aqueous mineral acid, adding the solution to Intralipid 10% ® (Cutter Laboratories, Berkeley, CA) and adjusting the pH of the resultant emulsion to the final pH with aqueous base. Of course, a water-soluble acid salt of HMM, such as HMM-HCl can be pre-formed and dissolved directly in water or in a volume-adjusted amount of the emulsion. The present HMM solutions do not comprise any toxic organic solvents, such as ethanol, benzyl alcohol, propylene glycol, dimethylacetamide or dimethylsulfoxide.

Using this protocol, final formulations containing dissolved concentrations of about 1-6 mg/ml, preferably about 3-5 mg/ml of HMM can be prepared. The administered unit or total dose will be selected by the clinician following staging of the cancer and evaluation of the physique and physical condition of the individual patient. However, as indicated by the Examples hereinbelow which describe the results of Phase I clinical trials, maximum-tolerated doses of about 500-600 mg/m$^2$/day (five days in a row every four weeks, continuing until patient is in regression or progression). The present HMM formulation preferably will be used in combination therapies, (with, e.g., cisplatin, cyclophosphamide, doxorubicin, vinca alkaloids and etoposide (VP-16). A number of specific combination therapies have been developed using oral HMM, and the present method of parenteral HMM administration can be substituted for oral HMM in these regimens. See, e.g., S. S. Legha et al, *Cancer (Phil.)*, 38, 27 (1976), the disclosure of which is incorporated by reference herein.

The invention will be further described by reference to the following detailed Example, wherein HMM was provided by the Drug Synthesis and Chemistry Branch, Division of Cancer Treatment, National Cancer Institute, Bethesda, MD. The internal standard, 2-Cl-(4,6-bis(dimethylamino))-1,3,5-triazine, was prepared at the Mayo Clinic, Rochester, MN. Melting points, NMR, and mass spectra were consistent with the published values in *J. Med. Chem.*, 10, 457 (1967). HMM for preparation of the parenteral formulation was provided by the Pharmaceutical Resources Branch, Developmental Therapeutics Program, Division of Cancer Treatment, National Cancer Institute. In addition to analytical data provided by the National Cancer Institute, identity and purity (>98%) of bulk HMM were determined by gas chromatographic and mass spectrometric analysis. Intralipid 10% ®, a fat emulsion consisting of soybean oil, egg yolk phospholipids, and glycerol and water, was purchased from Cutter Laboratories, Berkeley, CA. All other solvents and reagents were reagent or chromatographic grade.

EXAMPLE I—PHASE I CLINICAL TRIAL WITH INTRAVENOUS HMM.

A. Patients

Eighteen patients were treated on the one day every four weeks schedule and 28 patients were treated on the daily $\times 5$ four weeks schedule. Tumors included lung [8], colorectal [19], gastric [3], breast [3], ovarian [2], renal [2], bladder [1], parotide [1], hepatic [1], small bowel [2], thyroid [1], fibrosarcoma [1] and fibroblastic osteosarcoma [2]. Forty-five of 47 patients had received prior chemotherapy and/or radiotherapy. All patients had histologic or cytologic confirmation of unresectable cancer for which there was no conventional means of therapy that offered reasonable hope of cure or of significant palliation. All patients were ambulatory and in a reasonable state of nutrition. Patients were required to have WBC count $\geq 4,000$/mm$^2$, platelet count $\geq 130,000$ m$^2$, hemoglobin $\geq 10$ g/dl, serum creatinine $\leq 1.5$ mg/dl, ECOG performance status <3, fasting serum triglycerides $\leq 500$ mg/dl. Patients were excluded if they presented with uncontrolled infections, persistent (daily) nausea and/or vomiting, significant chronic obstructive pulmonary disease, any neurologic impairment, major surgery within the proceeding 30 days, radiation to >15% of the bone marrow within 30 days or radiation to total area >30% of bone marrow at any time.

Tests done prior to entry into study included a history, physical examination and tumor measurement whenever possible, WBC count, hemoglobin, platelet count, chest x-ray, electrocardiogram, electroencephalogram, urine analysis, triglycerides, SGOT, and serum creatinine. Between courses of treatment, the hematology group was checked twice weekly and the hemoglobin, SGOT and serum creatinine once weekly. Triglycerides were determined before and after each HMM treatment. Patients were entered in groups of three at each dose level. New patients were entered at a higher dose level only after the three patients treated at the previous level had been observed for a minimum of three weeks, counting from the last day of treatment. Patients not having significant toxicity at a given dose level were retreated at the next higher dose level but a minimum of three patients who never received HMM were entered at each escalation on each schedule. Dose levels on the daily $\times 5$ schedule were 10, 20, 40, 80, 120, 180, 270, 405, 506, 630, 945 and 745 mg/m$^2$. Dose increments for the one-day schedule were 360, 540, 675, 750, 844, and 1,000 mg/m$^2$.

B. Drug Preparation and Administration

Unit dose amounts of drug, Intralipid 10% ®, and diluents were changed as dose levels of HMM increased throughout the study. At doses which will be relevant for Phase II evaluation of the parenteral formulation, the following drug preparation scheme was employed. The Mayo Comprehensive Cancer Center Pharmacy weighed 500 mg portions of bulk HMM into sterile vials. HMM was dissolved in 0.1 N hydrochloric acid (sterile HCl for parenteral administration, USP) by adding 27.50 ml of the 0.1 N HCl to each 500 mg vial. The concentration of this solution was 18.2 mg HMM.HCl/ml. The volume of the HMM.HCl solution to be drawn up for each patient was determined by dividing the patient dose level by 18.2 (e.g., for a 750 mg dose, 750 mg divided by 18.2 mg/ml =41.2 ml of the HMM.HCl solution withdrawn from the vial). A 0.22 micron filter assembly was fitted to the syringe containing the appropriate HMM.HCl solution. The volume was filtered into a 500 ml empty sterile and sealed vial. Thus, the correct patient dose was placed in the evacuated vial. An equal volume of air was withdrawn from the sealed vial to maintain vacuum.

The amount of Intralipid 10% ® to be added was determined by dividing the dose by 5.1 (e.g. 750 divided by 5.1=147 ml). The appropriate volume of Intralipid 10% ® was added to the 500 ml vial containing the HMM.HCl solution. Finally, the volume of sodium bicarbonate (sodium bicarbonate for parenteral injection, USP, 1 mEq/ml) was determined by the formula of 0.1 ml sodium bicarbonate for every 20 mg of HMM to be administered (e.g., 750 mg divided by 20=37.5×0.1 ml =3.75 ml sodium bicarbonate). This provided approximately a 4 mg/ml solution of HMM-Intralipid 10% ®. A vented tubing set was added to the bottle with the patient's dose. A particulate filter (4.5 micron) was attached to an 18 gauge needle and the filter and needle were placed on the tubing to fill the 500 ml empty bag. The drug was administered at a rate of 2 ml/min or 8 mg/min. Thus, infusion time was lengthened as dose levels increased maintaining a constant rate of drug administration. Fifty (50) ml of normal saline was infused following completion of the HMM infusion.

Patients participating in the one-day schedule pharmacologic studies were hospitalized for drug administration and blood sampling. Four (4) ml of blood were drawn into heparinized tubes prior to drug administration at approximately equally spaced time points during the infusion and at 0, 5, 15, 30, 60, 90, 120, 240, 420, 720 and 1440 minutes following completion of the infusion. Samples were cooled, plasma obtained by low speed centrifugation and frozen (−20° C.) until analysis. Blood samples were also obtained from patients receiving HMM on the five-day schedule. One 4 ml sample of blood was obtained prior to drug administration on each day of the five-day regimen.

C. Gas Chromatography (GC) Assay For HMM

The nitrogen-phosphorous GC assay for HMM has been reported by M. M. Ames et al., *J. Chromatogr.*, 174, 245 (1979). Following addition of internal standard, plasma and urine samples were adjusted to pH 11 with 1 N NaOH, extracted with 6 ml toluene and 0.1 ml butanol, and concentrated to the butanol residue under a gentle stream of nitrogen. Aliquots of the butanol concentrate were injected for analysis on a silanized glass column (2 feet by 2 mm i.d.) packed with 10% Carbowax ® 20/2 KOH (Suppelco Inc., Belefonte, PA). An oven temperature program (170°-185° C., 10° C. per minute) was used for successive analyses, followed by 15-20 minutes at 190° C. to elute contaminants prior to injection of the next three samples. Drug concentrations were determined by comparison of drug/internal standard peak area ratios to those of standard curves prepared by addition of known amounts of HMM and internal standard to blood bank plasma.

D. Pharmacokinetic Analyses

Plasma HMM concentration data were analyzed using the NONLIN least-squares regression analysis program on a CDC Ciber 170-720 computer equipped with interactive graphic analysis. The triexponential decline of HMM plasma concentration was fitted to the equation $C=Ae^{\alpha t}+Be^{-\beta t}+ce^{-\gamma t}$ with a weighing factor of $1/Y$ where Y is the plasma concentration of HMM at time t following administration of the drug, A and B and C are intercepts at $t=0$, and $\alpha$ and $\beta$ and $\gamma$ are the disposition rate constants.

E. RESULTS 1. HMM Parenteral Formulation

Details of drug preparation are described in the Methods section while a summary of the formulation procedure is shown in Table 1, below.

TABLE 1.

| HM Formulation Procedure and Analysis of HMM in Solutions | | | |
|---|---|---|---|
| | | % Theoretical HMM Concentration | |
| Step | Theoretical HMM Concentration | Before Filter | After Filter[a] |
| Dissolve HMM in 0.1 N HCl | ca. 20 mg/ml | 100 | 100 |
| Add Intralipid ml 4 ml:1 ml Mix | ® | ca. 4 mg/ml | 10% 100 |
| Add NaHCO3 (1 mEq/ml) 0.1 ml:5 ml | ca. 4 mg/ml | 100 | 100 |

[a] 0.45μ filter

This modification of the initial formulation reported in *Cancer Treat. Rep.*, 66, 1579 (1982) to first dissolve the HMM in aqueous HCl, eliminated the use of a toxic organic solvent (ethanol or dimethylacetamide) while ensuring complete and uniform mixing of drug with Intralipid 10% ®. Assessment of the formulated product was determined at each step of the procedure by measuring HMM concentrations before and after filtration through 0.45 micron filters (Intralipid 10% ® average particle size is approximately 0.40 micron). As shown in Table 1, HMM concentrations obtained in the final filtered product were 90-95% of the theoretical value. If the product was prepared as described in Methods and summarized in Table 1 but distilled water, normal saline or dilute phosphate-buffered saline is substituted for Intralipid 10% ®, addition of the bicarbonate immediately yielded a flocculent while solid. HMM concentrations following filtration of such mixtures yielded <5% of the theoretical HMM concentration.

2. Toxicity

Two of 47 patients were inevaluable, one who progressed after the first treatment (one-day schedule) and did not return for further evaluation and one who developed a bowel obstruction after day two of the five-day schedule. There were no significant hematologic toxicities observed in any patient on the one-day or five-day regimen. One patient had a platelet nadir of less than 100,000/µl (75,000), that following one-day administration of 540 mg/m². There were no white blood cell counts below 3,000/µl.

The only non-hematologic toxicity, and the dose-limiting toxicity, was nausea and vomiting. The maximally tolerated doses of HMM on the one-day and daily ×5 schedules were approximately 850 mg/m² and 630 mg/m²/day, respectively.

Because substantial volumes of Intralipid 10% ® were administered to patients (but <500 ml daily for 5 days), triglycerides were determined before and after treatment courses. No significant increases were seen when comparing pre-treatment to post-treatment values.

3. Responses

No objective responses were seen in the 47 patients.

4. Pharmacologic Studies

Blood samples were initially obtained from patients receiving HMM on the one-day schedule in the outpatient clinic. Analysis of plasma HMM data showed that sampling would be better conducted with hospitalized patients in order to obtain samples for 24 hours following drug administration. Accordingly, blood samples were obtained from five patients who received 540 mg/m² on the one-day schedule. Plasma concentration-time profiles for these five patients are illustrated in FIG. 1. Peak concentrations of HMM at the end of infusion ranged from 2.55-9.35 µg/ml.

Plasma elimination was best described by a three-compartment open model with terminal elimination phase half-life, total body clearance and steady state volume of distribution values of 10.4 hr, 0.75 l/min/m², and 460 l/m², respectively. Twenty-four (24) hour urinary recovery of parent drug was <1%. Demethylated urinary metabolites including penta-, tetra-, tri-, and di-methylmelamines were detected in urine. Monomethylmelamine and melamine were not extracted by our drug isolation method.

Figure 2:
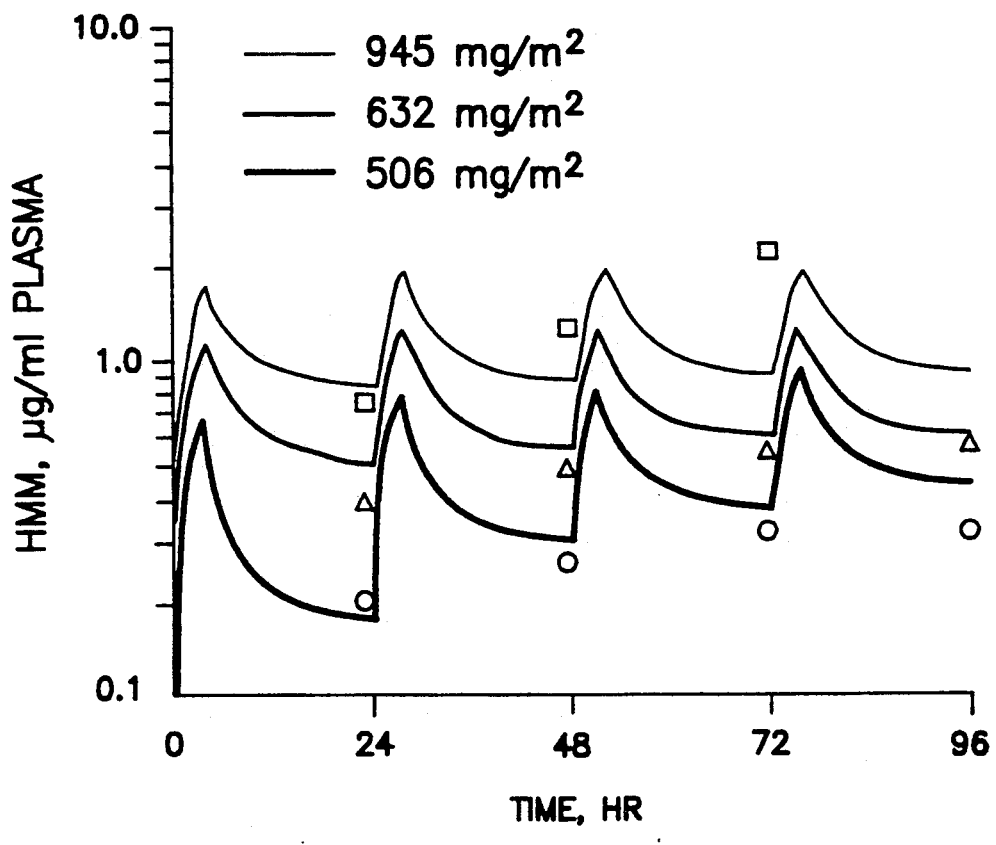
FIG. 2 is a graphical depiction of the plasma concentration-time profiles for patients receiving sequential doses of HMM.

HMM was detected 24 hours following each dose of drug on the daily ×5 schedule. The concentration of drug present in the 24 hour blood sample increased each day as well. Based on the pharmacokinetic analysis at the 540 mg/m² dose level, concentrations of HMM were simulated during the five days of treatment. The simulation curves and observed 24 hour HMM trough plasma concentrations are plotted in FIG. 2 for patients receiving 506, 632 and 945 mg/m². Observed plasma concentrations at the former two doses were in agreement with predicted values while observed concentrations were significantly greater than predicted for the 945 mg/m² dose level.

F. Discussion

Evaluation of potential antitumor of HMM activity may have been compromised by the unfavorable pharmacologic characteristics of HMM associated with oral administration. The formulation described herein was readily prepared by pharmacy personnel, provided 90-95% of the theoretical amounts of HMM in the parenteral formulation, and was well tolerated by all patients. No significant changes in serum triglycerides were associated with administration of the Intralipid 10% ®.

Drug-associated toxicities of HMM following intravenous administration were similar to those following oral administration with regard to the minimal myelosuppression and dose-limiting nausea and vomiting. However, no CNS toxicity, specifically peripheral neuropathy, was noted in any patients.

Intravenous administration of HMM provided more consistent plasma concentrations of HMM when compared to results following oral administration as reported by M. D'Incalci, in *Cancer Treat. Rep.*, 62, 2117 (1978). The bioavailability of HMM following oral and intravenous administration in patients has not been determined. Substantially higher plasma AUC values for HMM were found following intravenous administration when compared to oral administration, which is consistent with published data obtained using the rabbit model [M. M. Ames et al., *Cancer Res.*, 39, 5016 (1979)]. The disproportionate accumulation of HMM during five days of treatment observed in patients who received 945 mg/m² is consistent with a saturable component of plasma HMM elimination, which is probably related to hepatic N-demethylation.

The invention has been described with reference to various specific and preferred embodiments and techniques. However, it should be understood that many variations and modifications may be made while remaining within the spirit and scope of the invention.

What is claimed is:

1. A method for reducing the peripheral neuropathy associated with chemotherapy with hexamethylmelamine comprising intravenously administering a stabilized solution of an effective antineoplastic amount of hexamethyl-melamine (HMM) to a cancer patient in need thereof; wherein said HMM is dissolved in an aqueous emulsion comprising about 2-20% of an edible oil; about 0.1-7% of a phosphatide and about 1-10% glycerol, so that peripheral neuropathy is reduced from that observed when the same amount of HMM is orally administered.

2. The method of claim 1 wherein the pH of the HMM solution is about 4.5-6.0.

3. The method of claim 1 wherein about 500-600 mg/m²/day of HMM is administered.

4. The method of claim 3 wherein the HMM is administered in conjunction with an effective amount of cis-platin, cyclosphosphamide, doxorubicin, vinca alkaloids or etoposide.

5. The method of claim 1 wherein the edible oil comprises soybean oil.

6. The method of claim 1 wherein the phosphatide comprises egg yolk phospholipids.

7. The method of claim 1 wherein the HMM solution comprises about 1-6 mg/ml HMM.

* * * * *

UNITED STATES PATENT AND TRADEMARK OFFICE
CERTIFICATE OF CORRECTION

PATENT NO. : 5,004,593

DATED : April 2, 1991

INVENTOR(S) : Ames et al

It is certified that error appears in the above-identified patent and that said Letters Patent is hereby corrected as shown below:

Column 6, lines 28-43, delete in ties entirety "Table 1." and replace with the following:

Table 1. HMM Formulation Procedure and Analysis of HMM in Solutions

| Step | Theoretical HMM Concentration | %Theoretical HMM Concentration Before Filter | After Filter[a] |
|---|---|---|---|
| Dissolve HMM in 0.1 N HCl | ca. 20 mg/ml | 100 | 100 |
| Add Intralipid 10%® 4 ml:1 ml Mix | ca. 4 mg/ml | 100 | 100 |
| Add NaHCO$_3$ (1 mEq/ml) 0.1 ml:5 ml | ca. 4 mg/ml | 100 | 100 |

[a] 0.45 $\mu$ filter

Signed and Sealed this

Twentieth Day of October, 1992

Attest:

DOUGLAS B. COMER

Attesting Officer  Acting Commissioner of Patents and Trademarks

UNITED STATES PATENT AND TRADEMARK OFFICE
CERTIFICATE OF CORRECTION

PATENT NO. : 5,004,593

DATED : April 2, 1991

INVENTOR(S) : Ames et al

It is certified that error appears in the above-identified patent and that said Letters Patent is hereby corrected as shown below:

Column 6, lines 28-43, delete in ties entirety "Table 1." and replace with the following:

Table 1. HMM Formulation Procedure and Analysis of HMM in Solutions

| Step | Theoretical HMM Concentration | %Theoretical HMM Concentration Before Filter | After Filter[a] |
|---|---|---|---|
| Dissolve HMM in 0.1 N HCl | ca. 20 mg/ml | 100 | 100 |
| Add Intralipid 10%® 4 ml:1 ml Mix | ca. 4 mg/ml | 100 | 100 |
| Add NaHCO$_3$ (1 mEq/ml) 0.1 ml:5 ml | ca. 4 mg/ml | 100 | 100 |

[a] 0.45 μ filter

Signed and Sealed this

Eighth Day of December, 1992

Attest:

DOUGLAS B. COMER

Attesting Officer

Acting Commissioner of Patents and Trademarks